United States Patent
Vaudrey et al.

(10) Patent No.: US 6,396,930 B1
(45) Date of Patent: May 28, 2002

(54) ACTIVE NOISE REDUCTION FOR AUDIOMETRY

(76) Inventors: Michael Allen Vaudrey, 208 Northlake Rd., Columbia, SC (US) 29223; William Richard Saunders, 2509 Plymouth St., Blacksburg, VA (US) 24060

( * ) Notice: Subject to any disclaimer, the term of this patent is extended or adjusted under 35 U.S.C. 154(b) by 0 days.

(21) Appl. No.: 09/026,564

(22) Filed: Feb. 20, 1998

(51) Int. Cl.[7] .............................................. H04R 29/00
(52) U.S. Cl. ..................... 381/60; 381/71.6; 600/559
(58) Field of Search ...................... 381/60, 71.6, 71.7, 381/71.11, 72, 74; 73/585; 600/559

(56) References Cited

U.S. PATENT DOCUMENTS

| | | | |
|---|---|---|---|
| 3,647,969 A | 3/1972 | Arguimbau et al. | |
| 3,648,196 A | 3/1972 | Gay | |
| 3,793,484 A | 2/1974 | Feezor | |
| 3,793,485 A | 2/1974 | Feezor | |
| 3,809,811 A | 5/1974 | Delisle et al. | |
| 4,224,468 A | 9/1980 | Calder | |
| 4,768,165 A | 8/1988 | Hohn | |
| 5,197,332 A | 3/1993 | Shennib | |
| 5,481,615 A | * 1/1996 | Eatwell et al. | 381/71.6 |
| 5,721,783 A | * 2/1998 | Anderson | 381/316 |
| 5,815,582 A | * 9/1998 | Claybaugh et al. | 381/71.6 |
| 5,825,894 A | * 10/1998 | Shennib | 381/60 |
| 5,852,667 A | * 12/1998 | Pan et al. | 381/71.6 |
| 6,058,194 A | * 5/2000 | Gulli et al. | 381/72 |
| 6,160,893 A | * 12/2000 | Sauders et al. | 381/71.6 |

OTHER PUBLICATIONS

"Audiometric Ear Canal Probe with Active Ambient Noise Control", by Rafaely Boaz, *IEEE Transactions on Speech and Audio Processing*, vol. 4, No. 3, May 1996.

* cited by examiner

*Primary Examiner*—Xu Mei
(74) *Attorney, Agent, or Firm*—James W. Hiney (57) ABSTRACT

The technology of active noise reduction (ANR) is incorporated into audiometry testing in a variety of formats. Analog feedback, digital feedback, adaptive feedforward, and adaptive feedback noise control schemes are presented for use in audiometry to reduce the ambient noise heard by the test subject, allowing subject testing in higher ambient noise fields. Audiometer test signals are appropriately compensated so the test results are accurate and comply with existing calibration standards for audiometers. Existing audiometry headphone technologies are modified so that ANR can be accomplished while satisfying existing standards for audiometric testing. Embodiments are also defined for alternate headphone arrangements that may not conform to current (1997) audiometric testing standards but provide sufficient performance advantages to warrant new standards for audiometry testing in the future.

8 Claims, 5 Drawing Sheets

ACTIVE NOISE REDUCTION FOR AUDIOMETRY

FIELD OF THE INVENTION

This invention relates to the application of any one of a variety of ANR techniques to audiometry testing and to corresponding embodiments of audiometry testing headphones. Specifically, the reduction or cancellation of ambient noise of any spectral content existing in and/or around the vicinity of an audiometric testing facility is the main object of the invention. Audiometry testing stimuli are compensated in appropriate ways, after the application of the ANR method, resulting in accurate testing results that conform to standard calibration procedures. This invention includes the field of electronic equipment used for audiometry testing as well as the field of electronic devices used for personal ANR implementations.

BACKGROUND OF THE INVENTION

Audiometric testing requires very low ambient noise levels in order to determine a subject's hearing threshold level. (Ambient noise may refer to the noise heard by the user under the audiometric test headphones or to the noise in the immediate area surrounding the test subject. The specific meaning will be clear in the context of the subsequent discussion.) In the past, two methods have been used to achieve low ambient noise environments where test subjects can be accurately tested. Artificially quiet environments have been created by installing various sizes of soundproof testing booths (chambers or rooms) in locations that are otherwise too noisy. An alternative to this expensive option has been to add more passive attenuation materials to existing headphones, thus enclosing the ear in a chamber called a circumaural headphone architecture (such as the Audiocup). This option is not preferred by some audiologists because of non-uniformity of testing results caused by improper fitting of such headphones to the wearer. Recently, insert earphones were introduced into the industry as an alternative to booths and circumaural headphones. Although they are capable of providing accurate test results in higher ambient noise fields than most other test headsets, their low frequency insertion loss is unacceptably low for many noise fields. In addition, significant variability in testing results due to fitting issues has left a need to seek out new innovations for audiometric testing in noisy environments.

The use of ANR techniques to reduce the acoustic noise perceived by a human listener has become quite popular in the last ten years. There are numerous patents related to the art and many of those innovations are related to various configurations of ANR headsets. Although there are substantial variations among the different types of ANR headsets that are i existence, none of the headsets have been designed to be integral components in hearing evaluation equipment or for the purpose of improving the quality of audiograms generated in situ. The instant innovations significantly advance the state-of-the-art for ANR headphones, providing a completely new design process and fabrication than previously defined by prior inventors.

OBJECTS OF THE INVENTION

Accordingly, it is an object of this invention to reduce ambient noise in any audiometry testing environment, clinical or otherwise, by use of active noise control technology for the purpose of improving the accuracy of measured hearing thresholds in noisy environments and, It is another initial object of this invention to provide active cancellation of ambient noise in audiometry over a wide frequency range and, Yet another object of this invention is to provide for audiometric testing in high ambient noise conditions using active noise cancellation techniques and, It is another object of this invention to use feedback control with analog and/or digital hardware and/or software to implement the active noise control in an audiometer and, It is still another object of this invention to use feedforward control employing digital software and some external analog hardware to implement the active noise control in an audiometer and, It is a further object of this invention to use both feedback and feedforward control simultaneously to implement the active noise control in an audiometer thereby selectively canceling different types of noise and, It is yet another object of this invention to meet existing audiometry testing standards while incorporating active noise control into either a new or existing hearing testing device and, Still further, It is an object of this invention to use active noise control in a headphone or headset system that is also used to perform audiometry testing thereby performing the active noise control and hearing testing simultaneously and, It is a still further object of this invention to use the same or different actuator or actuators for delivering both the audiometry test stimulus and the active noise control signal and, Furthermore It is an object of this invention to deliver any audiometer test signal to the test subject while attenuating the ambient noise with active noise control, in such a manner that the test stimulus is either not affected by the control process or the test results can be interpreted so as to factor the controller into the results and, It is an additional object of this invention to deliver any audiometer test stimulus to the test subject through the same actuator or different actuators, while reducing the ambient noise using active noise control such that the nature of the test stimulus is independent from the control action and, It is yet another object of this invention to provide an external device which can be used with any existing audiometer and requires no modification in order to realize the benefits of active noise reduction to any existing audiometry hardware and, It is a final object of this invention to integrate the active noise control technology into a specially built audiometer that is either an existing audiometer that has been modified for the purpose of including the active noise control technology or an audiometer that is manufactured to have already incorporated in it, the active noise control technology.

DETAILED DESCRIPTION AND PREFERRED EMBODIMENT

A large number of applications of active noise control (ANC) have been confined to laboratory experiments performed under carefully controlled conditions. However, in the past decade, ANC has found a specific market in hearing protection devices. Headsets designed to protect the wearer from harmful sound pressure levels now incorporate both passive and active measures. Passive control (typically in the form of a circumaural cushion) is most effective at protecting the wearer from high frequency disturbances whereas active control is most effective for frequencies below 1 kHz. By placing the active noise control system inside the headset and close to the user's ear, manufacturers of these devices take advantage of a local zone of silence created around the error microphone, as well as minimal power requirements for the near-field architecture of ANR headsets.

While the hearing protection application of active noise control is quite useful, it does not constitute an object of this invention. Instead this invention seeks to utilize active noise control in hearing screening devices. Both the control objective and the specific application of ANC are different from the current state-of-the-art applications. In audiometry (or hearing screening), the objective is to deliver the audiometer test stimulus to the patient in a controlled setting so that the evaluation of the subject's hearing can be accurately ascertained. This differs from hearing protection where the goal is to reduce the amount of harmful noise that arrives at the user's eardrum. By including active noise control technology into audiometry, accurate hearing acuity tests can be given in higher and more diverse ambient noise fields than ever before. This technology will also permit many clinics and industrial hygienists to provide increased numbers of patients and employees with audiograms that meet stringent national and international standards.

The following descriptions provide many inventions and preferred embodiments of applying the ANC technology to audiometry and/or hearing testing devices. It is the intent of the inventors to provide many possible implementations for ANC in audiometry. Control systems, plant design and audiometer constructions are several of the main subject areas that are addressed. However, the primary focus of the invention is on the application of ANC to audiometry for the purpose of improving hearing testing procedures in a variety of environments.

The general technology of active noise control is well established and can be understood and implemented by those skilled in the art. Therefore, only a very brief description is provided. Active noise control uses an actuator, usually a speaker, to introduce into a noisy environment, a secondary sound pressure wave that is out of phase with the undesirable noise, or disturbance. The anti-wave is generated electronically with some control algorithm whose input is a measure of the disturbance field. This measurement is usually performed by a microphone. There are many configurations and designs for the control approaches that are application dependent. For the audiometry application, the goal is to provide a sound field at the user's ear that is quiet enough to measure a 0 dB hearing level (HL) for users with normal hearing acuity. In order to provide an accurate measurement, the audiometer must also provide a test stimulus with known SPL to the user's ear drum. Implementing ANC in a disturbance rejection format, effectively improves the signal-to-noise ratio (SNR) of the test stimulus to ambient noise by reducing the ambient noise instead of amplifying the signal.

Figure 1:
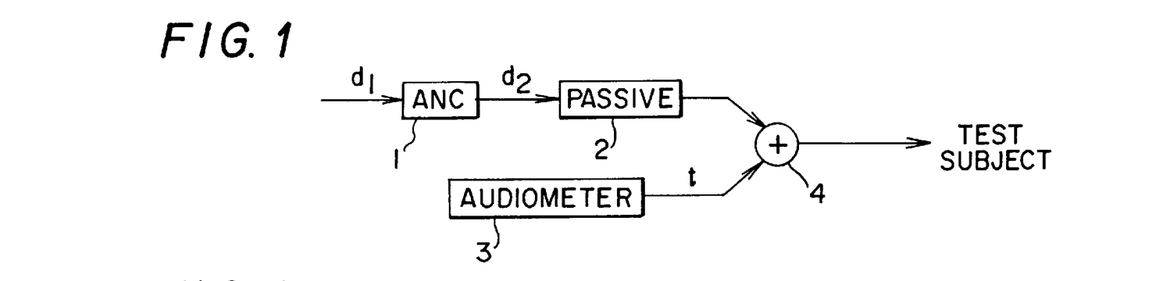
FIG. 1 illustrates the general inclusion of active noise reduction in audiometry in a manner such that each of the critical components stand alone.

State-of-the-art audiometry testing is performed using passive noise control devices to reduce the ambient noise to acceptable levels. These devices include insert earphones, test booths, supra-aural ear cushions and circumaural domes. The noise attenuation effectiveness of these devices monotonically degrades with decreasing frequency below 1 kHz, thus limiting severely the maximum ambient noise level in which accurate testing can be performed. By combining ANC with existing passive components, it will be possible to conduct accurate testing in higher ambient noise fields. FIG. 1 illustrates this concept. In order for the test stimulus to be delivered to the end-user without masking by the disturbance $d_1$, the passive performance (2) must reduce $d_1$ to an acceptable level. This effectively gives a maximum rating for the passive performance. When ANC is included (1), a higher ambient noise level $d_2$ can be tolerated because it can reduce the level to that of $d_1$ without any passive performance.

FIG. 1 clearly illustrates the four main components of this innovation. The passive performance (2) must work closely with the controller design and is often called the "plant". The plant design is discussed first, in detail, with specific reference to existing standards, passive noise control performance, and effects that the design has on active noise control in audiometry. Next, the controller (1) design is discussed. It can take on many forms including feedback, feedforward, and a combined feedback/feedforward approach. Next, the audiometer itself (3) may or may not be affected by the design of the controller and/or the plant. Methods for correcting any adverse effects are carefully explained since the audiometer must deliver the test stimulus to the user at a known SPL. Finally, the summing junction (4) in FIG. 1 is associated with the last component in the ANR audiometer design, i.e. the physical inclusion of the audiometer test signals in the ANR environment. Several methods for performing this task are presented.

In any control system, the "plant" is the system that the control acts upon. It includes all dynamics that exist between the output of the controller and the input to the controller. The plant is as critical to the control system design as the controller itself. Therefore, special emphasis is placed on the audiometry plant before discussing any controller approaches. First, consider FIG. 2a. Disregarding the control components for a moment, the passively controlled audiometry plant includes the input from the audiometer (6) (test stimulus) that drives the headphone speaker (7), the ambient noise disturbance d that is reduced by the passive control measure (5), the test subject's pinna (9), earcanal (9), and eardrum (10), and the test subject's response (12) detected by the audiometer. As mentioned earlier, a sensor is necessary to detect the disturbance so that the ANR control system can generate the anti-wave. Without loss of generality, it will be assumed that the sensor is a microphone placed near the subject's eardrum. This microphone placement is critical for many reasons that will be addressed momentarily.

Figure 2A:
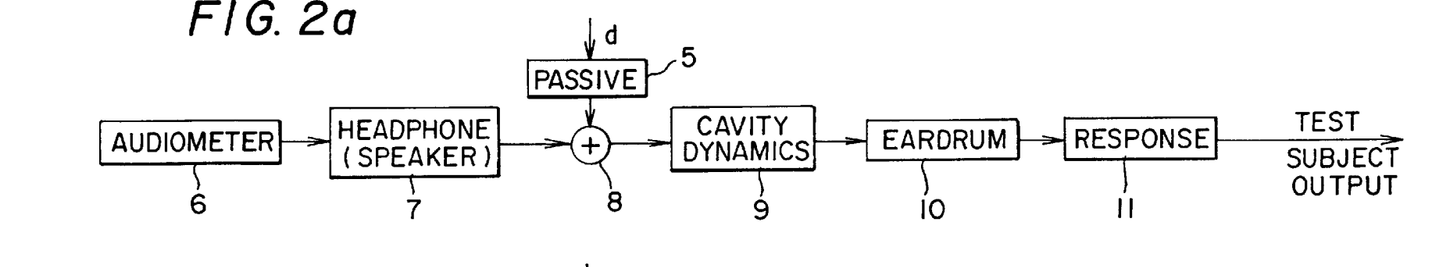
FIG. 2a shows a conventional audiometry testing system in block diagram form.
Figure 2B:
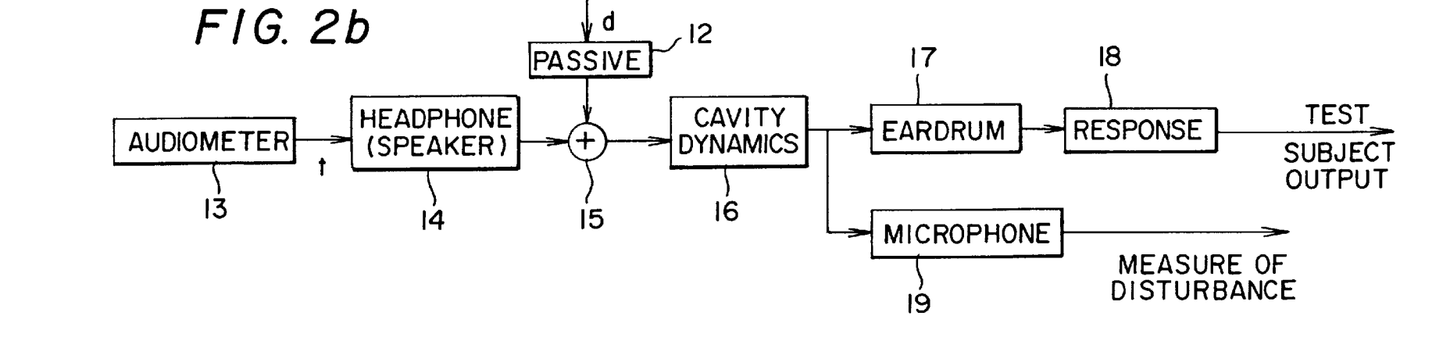
FIG. 2b shows the same conventional system with a quantitative measure of the sound reaching the test subject's eardrum.

Now consider FIG. 2b, the audiometry plant that includes necessary control components. The primary difference in FIG. 2a and 2b is that there is an additional output (19). The common output shown in the two figures (the test subject output (11)(18)) is simply a qualitative measure of the subject's response to the audiometer stimulus signal. The new output in FIG. 2b is a quantitative measure of the sound pressure level inside the cavity created by the headphone and the subject's pinna. This measure is a linear combination of the passively controlled (12) disturbance and the test stimulus at the location of the microphone (19). It is clear that the microphone signal provides the input to the controller. By tracing the propagation of the controller output signal, the plant can be defined. Without loss of generality, the output of an ANC controller is typically used to drive an electro-acoustic device such as a speaker. In this initial discussion it will be assumed that the headphone speaker (14) shown in FIG. 2b will also be used as the control actuator. Therefore the plant can be defined as the signal path including the dynamics of the headphone speaker (14), the cavity dynamics (16), and the microphone (19). Appropriate amplification of the controller output and microphone signals is also necessary but not mentioned here.

Figure 3:
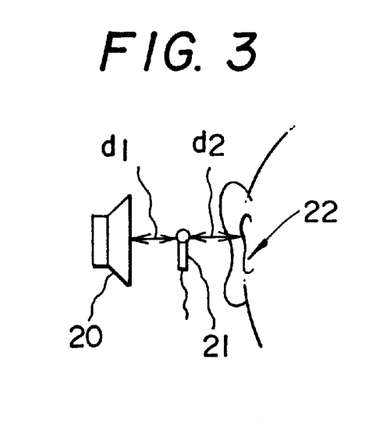
FIG. 3 illustrates a generalized relationship between the actuator, sensor and user for an active noise control application where the exact location of the microphone is a function of both the distance from the speaker and the distance from the user.

The microphone should be placed as close as possible to the subject's eardrum and as close as possible to the speaker. In order to satisfy both conditions, the speaker needs to be located very close to the subject's ear. FIG. 3 illustrates an example of this concept with a speaker (actuator) (20), microphone (sensor) (21) and subject (22). Distance $d_1$ is small enough to be in the acoustic near field of the speaker (less than the radius of reverberation) while $d_2$ is small enough to be less than the radius of the area of silence so that the highest desired frequency of noise reduction is perceivable by the test subject. Therefore, each of these distances is a function of the speaker size and ear canal depth, respectively.

Figure 4A:
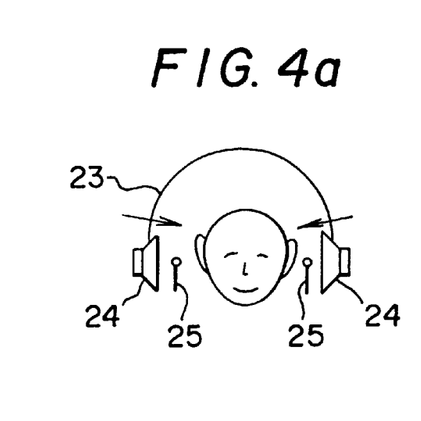
FIG. 4a shows a headphone implementation for the active control components used in audiometry where the actuator delivers both the test stimulus and the control force.
Figure 4B:
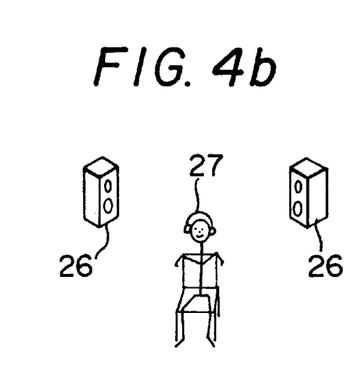
FIG. 4b illustrates one possible embodiment where separate actuators are used for test stimulus delivery and noise control.

Returning to the general arrangement of ANC, several options still remain for both actuator and sensor placement. For the descriptions presented above, both the actuator and sensor were fixed relative to the subject's head. This is typically in the form of a headset with a headband retaining both the left and right actuators. In the field of audiometry, this headband secures the headphone speakers onto the subject's ears with a specified force thereby creating a cavity in which the microphone sits. While it is clear that the microphone should be near the user's ear for reasons addressed above, it is possible that the actuators (speakers) could be located elsewhere. If these actuators were not affixed with respect to the sensor (affixed with respect to the user's ear), the plant dynamics could and would change with significant movement by the subject. In some fixed-gain control methods this change cannot be accounted for and performance will suffer. However, if the user were instructed to remain still during the testing procedure, ANC performance could be realized without affixing the control actuators to the user. Therefore, either affixing the control actuator (speaker) to the user or allowing the actuator to be fixed elsewhere in the environment are both viable options for actuator location. These are shown in FIGS. 4a and 4b. FIG. 4a uses two headphone actuators (24) that deliver both the control signal and audiometer test stimulus simultaneously, a sensor for each ear (25), and a headband (23) which secures the actuator sensor pair to the ears of the test subject. FIG. 4b uses two actuators: one for test stimulus delivery to each ear (27) and one set (26) for the active noise control force for each ear.

Figure 5:
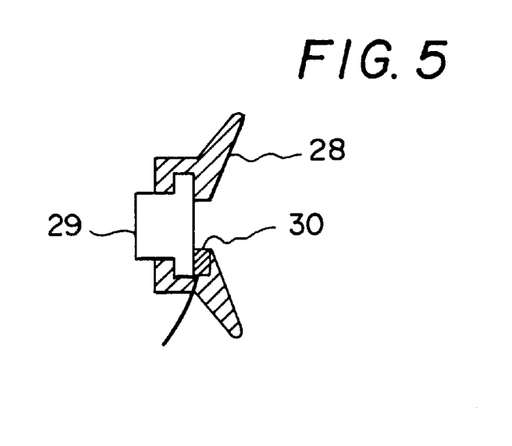
FIG. 5 shows one possible position for the error sensor required for active noise control in a standard audiometry test headset such that the inclusion of the sensor has no physical affect on the calibration procedure or normal fit of the cushion to the test subjects pinna.

There are currently two popular methods in audiometry for delivering the test stimulus to the subject at a known SPL: the MX-41/AR type cushion with TDH-# type speaker and the insert earphones. For this invention, each of these actuators can be used for control and test stimulus delivery, simultaneously. (This is discussed in more detail in further embodiments). This invention uses standard audiometry equipment to fit within the currently established national and international standards for audiometry testing devices; however, it would also be possible to realize the invention using speaker, earcup, and ear-cushion models that are not commonly used in modern audiometry test equipment. No standards preclude the use of ANC in audiometers but ISO 389 and ANSI S3.6 set forth very stringent requirements for calibration and design of the audiometer headphone and cushion. (The insert earphone is still being evaluated because it does not comply with either of these standards. By incorporating a microphone into the standard headset, the standard actuator can be used along with the passive measures (MX style cushion) to perform ANC without deviating from the regulations. For this specific arrangement, the microphone must be placed so that the required volume of contact during the calibration procedure (6 $cm^3$) is not reduced by the presence of the microphone. One possible headphone arrangement that meets ANSI and ISO standards is shown in FIG. 5. The cross-section of a TDH headphone (29) equipped with a microphone (30) and MX cushion (28) places the microphone such that the calibration volume is the same before and after insertion of the microphone. There are many more possible arrangements that will meet the current audiometer standards by ensuring a proper cushion, seal, and calibration procedure. They are not discussed in detail here but can be inferred without deviating from the general concept of permitting a proper calibration procedure with a microphone affixed to the headset near the speaker and/or near the subjects ear. It is envisioned that any such arrangement of the microphone, actuator and cushion which conforms to currently existing standards (1997) for audiometer headphones, will be claimed.

The insert earphones require a slightly different approach if ANC is to be used directly with the insert earphone actuator. The earphones fit into the subject's ear canal with a tube delivering the test stimulus to the eardrum. This method provides block low frequency disturbances and is plagued with user variability as a result of non-repeatable insertion depths. This drawback aside, it is possible to place a microphone inside the foam plug that is inserted into the subject's ear. This is all that is required to perform active noise control with the foam plug. (The different control approaches are discussed shortly).

Figure 6:
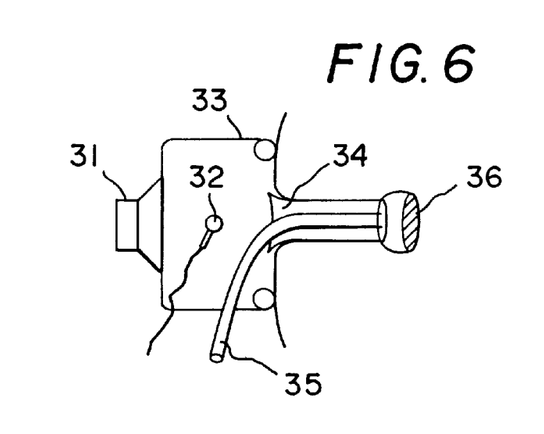
FIG. 6 illustrates another possible implementation where two actuators can be used, one for test stimulus delivery and one for control force delivery. In this figure the test stimulus is delivered by an insert earphone and the control force is included in a circumaural ANC headset device designed to minimized ambient noise for the purpose of performing audiometry testing.

A further embodiment that is envisioned for the application of ANC to audiometry involves using separate actuators for control and test signal delivery. The test signal actuator can be placed on the user's ear in accordance with the current standards. Then, an active noise control actuator-sensor pair can be placed in parallel with the test stimulus actuator. As will be seen later, depending on the control approach used, the test stimulus will likely be modified by the action of the controller. Using separate actuators can complicate the procedure required to compensate for this modification. This is explained in detail in the section describing the inclusion of the audiometer test stimulus. While this embodiment is not limited in application to either of the two traditional audiometer headphone devices, it will be most easily and effectively implemented with the insert earphones. FIG. 6 shows one possible embodiment of the dual actuator approach described above. The insert earphone (34) is used to deliver the test stimulus (35) directly to the subject's ear drum (36) and is effectively reducing ambient high frequency noise. Now, an active noise control headphone (33) having its own actuator (31) and sensor (32), is placed on top of the subject's pinna in order to provide low frequency attenuation. As mentioned above, compensation of the test stimulus is necessary in some control approaches, specifically feedback control. However, using separate actuators for insert earphone audiometry does not require test stimulus modification. This is considered to be a significant advantage. The reason for this is that the transfer function magnitude between the actuator delivery and the active noise control sensor is so small that the feedback control will not affect the test stimulus. This is shown in mathematical detail when the audiometer test stimulus delivery is described.

Figure 7:
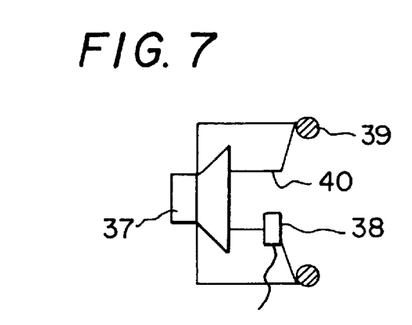
FIG. 7 shows one possible actuator, sensor, and passive noise control configuration that does not meet the current standards for audiometry due to the cicumaural cushion, but may provide excellent performance if the proper calibration procedure is specified.

Although the constraints of the standards for test stimulus delivery have been compatible with the previously described innovations in active noise control for audiometry, it is a further embodiment of this invention to provide a generic audiometer which incorporates active noise control without necessarily meeting applicable standards. A headphone system that has superior passive performance and incorporates active noise control, can be designed to deliver a known SPL to a subject's eardrum. The cross section of one such device is shown in FIG. 7. A larger volume (40) is provided to easily house the ANC sensor (38) and to bring it equally close to the subject's ear and speaker. A circum-aural passive seal (39) is provided which more effectively attenuates high frequencies than the conventional supraural cushion. A design such as this will improve both active and passive performance but will likely not meet applicable standards due to the circum-aural contact and excess volume in front of the speaker. However, a new calibration procedure is proposed for this system by first determining the average subject's eardrum location and enclosed volume. Then each test tone can be calibrated with an SPL meter located at the virtual average eardrum in a fixture that approximates the average human skull, pinna, ear canal combination. This is precisely the same Procedure used to calibrate the current standard; it is simply an estimate of the average human's auditory frequency response characteristics.

Until now, only embodiments of possible plant arrangements for ANC in audiometry with limited mention of controller architecture have been addressed. Although the physics of global and local noise control apply across all controller designs, certain controllers perform more effectively within these physical constraints than others, depending on the situation. The control strategies for audiometry described next do not disallow any type of active noise control technologies for the application of ANR audiometry. Each has advantages and disadvantages in different plant arrangements and noise fields. It is for this reason that plant dynamics and the physics of active noise control were discussed first. There are three different types of control that can be used for ANC in audiometry. They include feedback, feedforward, and combined feedback/feedforward. The preferred embodiments will now be discussed in this order. Once the general form and function of each controller is described, several of the plant options will be presented in terms of their effects on the controller design.

Figure 8:
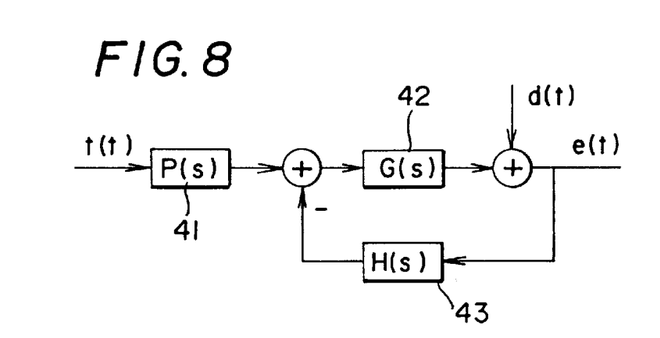
FIG. 8 is a general feedback control block diagram designed for disturbance rejection.

As mentioned earlier, the controller implementation is not intended for hearing protection but rather for disturbance rejection in relatively low noise environments encountered most often during audiometry testing. Feedback control approaches are well-suited for this type of control goal. FIG. 8 illustrates a block diagram of a conventional feedback control loop. The plant G(s) (42) contains all of the dynamics described earlier for the active noise control system while H(s) (43) represents the controller itself. The disturbance d(t) represents the undesirable ambient noise entering the system just following the plant. Finally the input signal t(t) is the test stimulus generated by the audiometer. It is modified by the pre-filter P(s) (41) before being delivered to the user via the plant. The output e(t) of the entire (closed-loop) system represents the sound pressure level experienced by the user and is also the input to the controller.

The feedback controller design itself is quite simple. Each transfer function in the block diagram is a function of frequency, represented using the Laplace variable "s". A mathematical expression for the time signal e(t) as a function of the signals d(t) and t(t) can be created assuming negative feedback and is shown below.

$$e(t) = \frac{G(s)}{1+G(s)H(s)}P(s)t(t) + \frac{1}{1+G(s)H(s)}d(t)$$

Examining the effects of the disturbance on the error signal, it is easily seen that by raising the overall gain of H(s), the contribution of the disturbance acoustic noise to the error signal is decreased. This is in fact the desired goal. There are limitations on the magnitude of frequency dependent gain that can be realized for the closed loop feedback controller. Adhering to Bode gain and phase margins, it is necessary to limit the open loop gain (G(s)*H(s)) in order to avoid adding noise to the system, thereby increasing e(t). These constraints are widely known within the control community and will not be discussed here. The primary difference in this innovation versus other feedback control designs is that the control goal of disturbance rejection is targeted toward extremely accurate delivery of the audiometry stimulus rather than hearing protection, thereby differentiating this invention from all other ANR headset applications. Technically, this differentiation is embodied in the specific design for F(s) and the specific form of H(s).

As mentioned earlier, and can be seen in the above equation the test stimulus is adversely affected by the closed loop system. It is desired to have the coefficient of the test stimulus t(t) equal to unity for all frequencies so the SPL delivered to the subject (e(t)), is known. In order the test stimulus must be designed to conform to the following equation:

$$P(s) = \frac{1 + G(s)H(s)}{G(s)}$$

Depending on the nature of the test stimulus, this equation can be satisfied for all applicable frequencies. In general, P(s) shown above will represent an acausal or unrealizable filter with a zero-pole excess. However, over the bandwidth of the test stimulus, a filter can be built that minimizes or eliminates the control loop's effects on the test stimulus. This is achieved by designing P(s) as shown above, over a narrow bandwidth of the test stimulus and subsequently adding higher (outside the test stimulus bandwidth) frequency poles.

Figure 9:
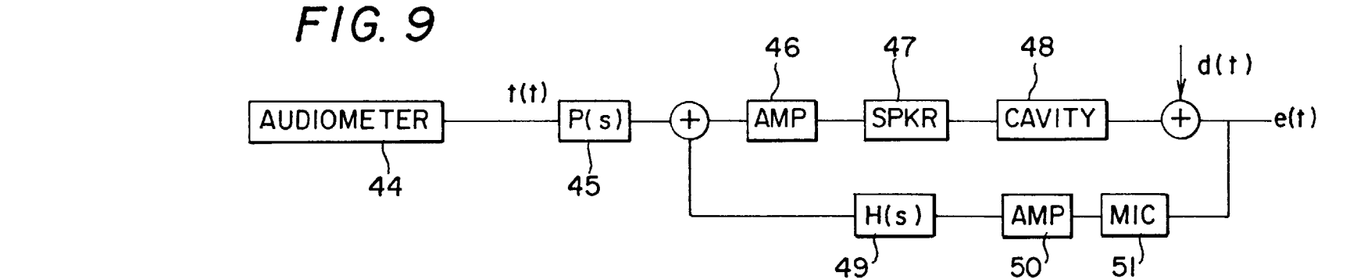
FIG. 9 is a more specific illustration of how analog feedback control can be used to reject ambient noise in an audiometer system.
Figure 10:
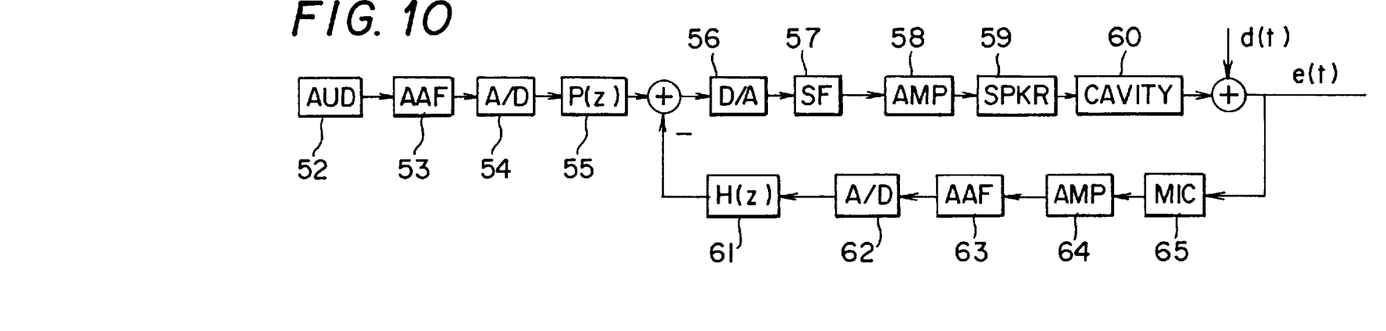
FIG. 10 is a similar embodiment to that of FIG. 9, but implements the feedback controller using digital components as well as analog components

The controller H(s), can be physically implemented in two possible realizations. FIG. 9 shows a detailed block diagram of a closed loop feedback controlled system for disturbance rejection in audiometry using analog electronics only. The analog filters P(s) (45) and H(s) (49) are built using operational amplifiers, resistors, and capacitors to place the zeros and poles of P(s) and H(s). The components include signal amplifiers (46)(50), the speaker (47), microphone (51) and cavity (48). FIG. 10 shows an entirely different implementation of feedback disturbance rejection for audiometry, realized using digital software. H(z) (61) and P(z) (55) are digital filters designed under the same Bode gain and phase constraints discussed above, implemented using FIR or IIR filters in DSP software. However, the plant now includes additional hardware necessary for performing digital control. Anti-alias (53)(63) and smoothing (57) low-pass filters are necessary to eliminate higher frequencies that may alias as a result of sampling. Adding these components into the feedback loop introduces additional dynamics that can make controller design more difficult and less optimal than that which can be achieved using analog components. However, the ease of digital design changes, added features, and software monitoring options in audiometry makes digital feedback control an attractive option. This versatility is more readily available when implementing feedforward control in audiometry disturbance rejection.

Figure 11:
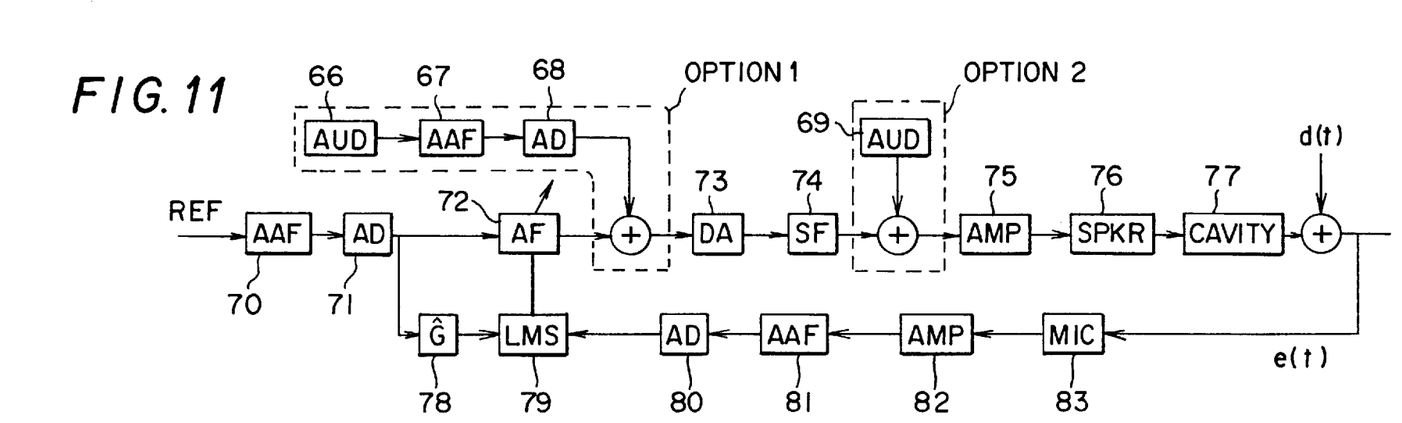
FIG. 11 illustrates feedforward noise control for use in rejecting ambient disturbances in audiometry while also offering two possible options for delivering the audiometer test stimulus.

Proper designs of feedforward control use signal information other than the error sensor as an input to the controller. Therefore, feedforward control is not subject to the same stability constraints specified for feedback control. FIG. 11 illustrates the feedforward control approach for active noise control in audiometry. Because of the complexity of the algorithm it is not possible to efficiently implement the feedforward controller using only analog hardware, so only the digital implementation for audiometry is shown. Beginning with the controller itself (72)(79), the general structure is commonly known as the filtered-X LMS algorithm used in active noise control. The software based algorithm (79) computes the weights (filter coefficients) for the FIR filter (72) using either the standard LMS algorithm or the "leaky" LMS algorithm, shown respectively below $$\hat{w}(n+1) = \hat{w}(n) + \mu r(n) e^*(n)$$

$$\hat{w}(n+1) = (1-\mu a)\hat{w}(n) + \mu r(n) e^*(n)$$

where the weights (w(n)) are calculated during each sample iteration based on the measurement of the reference signal r(n) and the error signal e(n). The error signal is the same as in feedback control, collected from the error sensor (microphone) (83) near the subject's ear. The reference signal, however, is a signal that is highly correlated with the error signal but not controllable by the control actuator, or speaker (76). (This prevents a feedback loop that can go unstable). The selection of this reference signal for active noise control is most commonly a secondary microphone located at a distance far enough away from the speaker that the frequency response function magnitude from the speaker to the reference microphone is lower than −20 dB at all frequencies. The exact location of a microphone that satisfies this requirement must be established for a particular implementation and is dependent upon the speaker size and noise field. In both the normal LMS and leaky LMS algorithms the factor R controls the rate of convergence of the filter and should be less than the inverse of the average reference signal power. This constitutes the stability constraint in feedforward control. If this value is too high the algorithm will diverge by taking too large of an increment between weight calculations. If it is too small, convergence will not be fast enough for changing noise field dynamics. Finally, the "forgetting factor" in the leaky LMS algorithm allows old non-useful weight update information to be lost over time. This is useful when transient noises impinge on both the reference signal and the error signal but need not be controlled over long periods of time.

The weight update equations shown above can be solved for the optimal Wiener solution for linear filtering. For ideal conditions (i.e. no noise) this optimal solution corresponds to the matrix multiplication of the inverse autocorrelation matrix of the reference signal and the cross correlation matrix of the reference-to-error signals. Given this, any signal that is present in the error but not in the reference (or vice versa) will have a very small cross correlation and will therefore not be controlled. This is ideal when including the audiometer signal in the feedforward control approach because no external modification to the test stimulus is necessary in order to provide the test stimulus to the user unaffected by any control action. This holds true whether the stimulus is presented through the same or different actuators as the control signal, as long as it is not present in both the reference signal and the error signal.

There are three possible alternatives for the inclusion of the audiometer test stimulus into the feedforward control algorithm if only one actuator is used simultaneously for both control and test stimulus. Two of these are explicitly shown in FIG. 11 as "Option 1" and "Option 2". The first option uses the same DSP that is running the control code, to sample the signal (68) exiting the audiometer (66) (with the appropriate anti-alias filter (67) in place). This permits the algorithm to add the two signals together in the software, and drive the single actuator (76) with both the control and test signals. The second option shown in FIG. 11 incorporates an analog-based summing amplifier just before the speaker amplifier so that the audiometer (69) signal can be added to the control signal. This combined signal is then used to drive a single actuator (76) that delivers both the control and test stimulus. The third and final option (not explicitly shown) for delivery of the test stimulus is to generate the stimulus from within the control code and add it to the computed control signal. This provides the most flexibility for inclusion of software analysis, display, and control options and allows the DSP to perform the entire ANC audiometry task.

In general, feedforward control is most effective for controlling tonal sound fields because the correlation between the reference signal and error signal is highest for sinusoidal waveforms. Since conventional feedforward control is not bounded by the stability constraints of feedback control, theoretical performance is only limited by the correlation between the reference and error signals. For very high coherence, feedforward performance is unbounded. Feedback control however, has limited levels of performance over a pre-specified bandwidth as determined by the Bode gain phase relationship. For these reasons, feedback control tends to perform better for broadband and "flat" noise fields while feedforward control performs better for tonal noise fields. In reality, most ambient noise fields contain a combination of broadband and tonal content. Therefore, the best choice for a controller that can effectively reject these disturbances is a combination of feedback and feedforward control. The audiometer application may require the blended approach depending on the ambient noise environment, so it is specified in this description.

Figure 12:
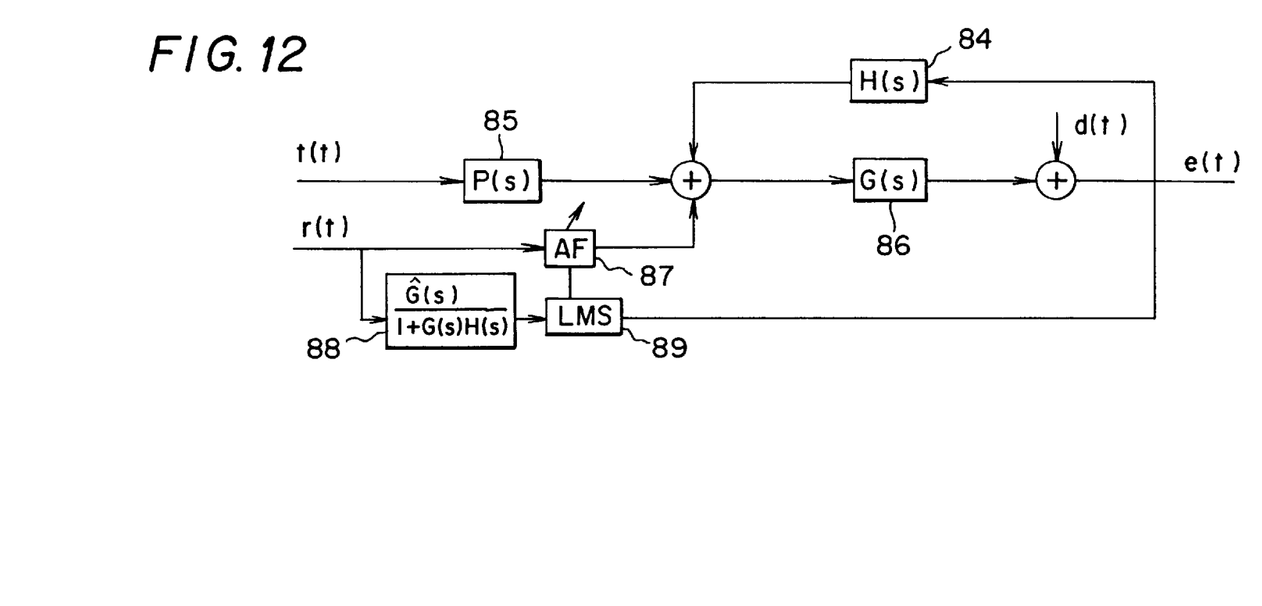
FIG. 12 illustrates combined feedback and feedforward active noise control for use in rejecting ambient noise during audiometry testing.

FIG. 12 illustrates a block diagram of the combination feedback and feedforward control approach for audiometry. Several of the details presented for the individual control approaches still apply to FIG. 12 even though they are not explicitly shown. (These include the microphone, amplifiers, cavity and speaker represented by G(s) (86) and the anti-alias and smoothing filters required in the sampling process). In order to combine these two control approaches the feedback controller (84) must be in place before the feedforward controller (87)(89) is designed. This is primarily because the system identification required by the filtered reference (88)LMS algorithm (89) changes when the controller is included in the loop. (Although FIG. 12 shows the feedback controller in an analog implementation, the combined controller can also be entirely digital). Once the feedback controller has been designed for disturbance rejection, the system ID for the feedforward controller can take place. During control, the output of the feedback controller is added directly to the output of the feedforward controller to form a single control signal that is sent to the actuator. The test stimulus is also combined with the control force and sent to the same actuator if only a single actuator is used for both control and test signals. The pre-filter (85)for the test stimulus is to compensate for the feedback portion of the combined controller only. As mentioned earlier, the feedforward control approach has no effect on the test stimulus as long as it is not present in the reference signal.

Returning to FIG. 1, the final design embodiments focus on the summing junction (4) that includes the audiometer (3). Thus far, there has been no discussion of the physical arrangement of the audiometer with respect to the ANC hardware. Next the inclusion of the unaffected audiometer signal for all proposed plant and control options will be reviewed. Then, two embodiments of the ANC audiometer will be described in terms of locating the ANC hardware and/or software with respect to the audiometer hardware and/or software.

As mentioned earlier, feedback control can and will adversely affect the test stimulus once the loop has been closed. In the case where only one actuator is used for control and stimulus delivery, the two voltages are combined using a summing junction realized in analog hardware (operation amplifiers) or in digital software code. Already discussed in detail, the pre-filter necessary for the test stimulus must cover the same bandwidth as the test stimulus and invert the closed loop control system to ensure that the test stimulus remains unaffected.

Figure 13:
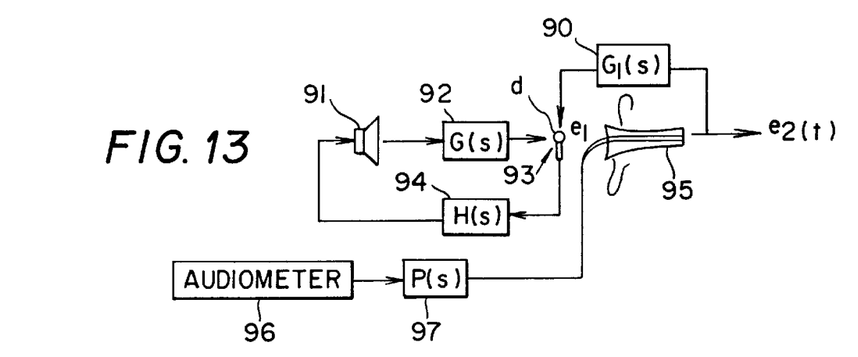
FIG. 13 assists in the derivation of the test stimulus prefilter required for the system shown in FIG. 6 where a separate actuator is used to deliver the test stimulus and the control force.

In the case where two actuators are used, one for the control and one for the stimulus, the required pre-filter becomes a function of the dynamics between the actuator delivering the test stimulus and the error sensor in active noise control. This can be seen by considering FIG. 13 for the case where the insert earphone (95) delivers the test stimulus and a separate actuator (91) delivers the active noise control signal. There are actually two error signals which can be evaluated: the active noise control sensor (93) and the sound pressure level at the eardrum $e_2(t)$. Using the block diagram in FIG. 13, the signal at the subject's eardrum (which is of primary concern) is represented by the following equation.

$$e_2(t) = \frac{1 + G(s)H(s)}{1 + G(s)H(s) + G_1(s)} P(s)t(t) + \frac{1}{1 + G(s)H(s) + G_1(s)} d(t)$$

In general, the test stimulus behaves as part of the disturbance that the closed loop controller is attempting to cancel. However, if $G_1(s)$ (90) is very small, the transfer function coefficient becomes unity and the pre-filter P(s)(97) can also be unity in order to deliver t(t) to the eardrum unaffected. This illustrates a clear advantage for using separate actuators as long as the transfer function (90) from the stimulus delivery to the error sensor is assumed small. In cases where $G_1(s)$ is not small, two actuators can still work but P(s) is non-unity and must be designed to invert the coefficient of t(t) in the equation above, over the bandwidth of the test stimulus. These conclusions are generalized for the case of two actuators used in feedback noise control using the equation above.

Feedforward control offers a distinct advantage over feedback for ANR audiometry in that the test stimulus can be delivered to the subject unaffected by the control action, without any additional modifications. As discussed during the plant design section above, the error sensor (microphone) should be located close to the subject's ear to maximize noise control performance. Given this, whether one or two actuators are used in feedforward control, the error sensor will detect at least some of the test stimulus as it is delivered to the subject. However, as long as the reference sensor does not detect or contain signal content from the test stimulus (i.e. coherence is low), the feedforward controller will have no effect on the test stimulus. For this reason, the combined feedback and feedforward control option will only require modification as a result of the feedback control force, and not the feedforward. In the case of two actuators and combined feedback and feedforward control, the equation above will apply since the feedforward control action will have no affect on the test stimulus.

There is one final alternative for delivering the audiometer test stimulus during control. The primary requirement for delivery of the test stimulus is that the SPL at the eardrum needs to be known. This allows an accurate comparison of hearing levels to those with normal hearing at 0 dB HL (established over many years of testing). The goal of modifying the test stimulus with a pre-filter is to deliver the signal without modification so calibration baselines can be established as they always have been. However, since calibration of the audiometer must occur before each hearing test, the baseline could be established for the test stimulus during the calibration procedure, thus eliminating the need for a pre-filter. This works especially well for narrow band test stimuli such as pure tones. An example of this is now presented for clarity.

Consider that single actuator, single sensor ANC audiometry is performed using feedback control for disturbance rejection. The pre-filter required for a pure tone test stimulus is one frequency unit wide and corresponds to a simple gain. With the pre-filter in place, the calibration setting for the pure tone under test, before and after the inclusion of the ANC will not differ since the SPL of the tone has been adjusted to remain the same. However, if the pre-filter is removed, the SPL of the test stimulus will be much lower due to the closed loop control action. Calibration of the SPL of the test tone will be different for the control on vs. control off case. If the test tone is reduced by 20 dB due to the control action, the calibration of the measured hearing level can be adjusted by adding 20 dB, thus eliminating the need for a pre-filter. For broad band test stimuli such as speech, the calibration procedure will not be as effective in determining accurate thresholds due to the need for frequency dependent gain.

Once the test signal has been included into the control algorithm, a decision must be made on how to properly incorporate the audiometer hardware or software with the ANC hardware or software. There are several possible embodiments that are now discussed.

Figure 14:
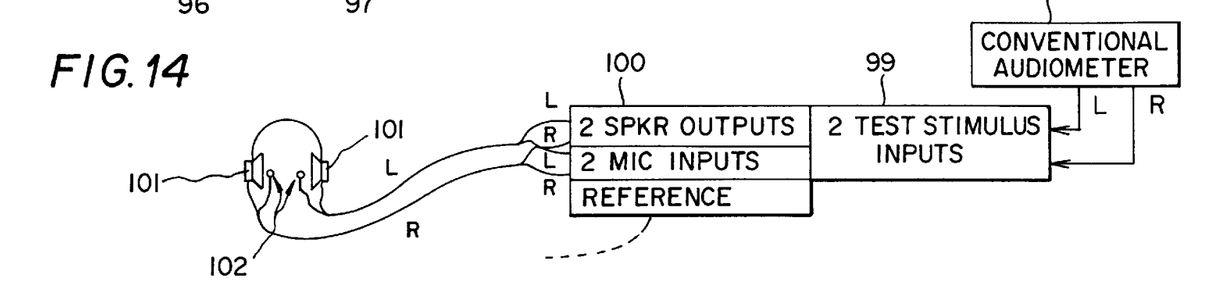
FIG. 14 shows the generalized design for a retroactively fit active noise control device which can be used with any audiometer.

Many fully functional audiometers currently exist and are used in clinics, industrial settings and offices around the world. The most common design of these audiometers consists of a headphone system that can be easily disconnected from the audiometer hardware that generates the test stimulus and receives an indication of the patient's response. Because of this modular design, it is easy to provide a retroactively fitted ANC device that works in conjunction with current audiometer hardware. FIG. 14 illustrates one possible embodiment of such a device. The ANC retro-fit device includes the ANC headphone system (101)(102), an input output device (100)(99) containing the ANC hardware or software (depending on the control approach used), and two cables to connect the standard audiometer to the ANC device. In most audiometers (98), the left and right ear testing cables are separate one-channel lines (as opposed to a single two-channel line). Either embodiment is possible depending on the output of the audiometer. The ANC device receives as its input, the left and right audiometer signals that are sent to the pre-filters (if required) as described above. These signal inputs must be impedance matched.

The stimulus delivery system cannot be the conventional headphone system delivered with the standard audiometer. The headphone system (101)(102) will conform to the plant design requirements presented above for ANC audiometry, but may be any embodiment that has been described and still apply to this retro-fit device. There are two other inputs and two outputs for the retro-fit ANC audiometer. The two inputs are the left ear and right ear microphones (102) and the outputs are the left ear and right ear actuators (101). If a dual actuator approach is used, the test stimulus can either be pre-filtered by the ANC device (requiring two more outputs) or passed directly to the test stimulus delivery actuator if pre-filtering is not required. Other inputs to the ANC retro-fit device could include a reference signal for use in feedforward or combined feedforward and feedback control. This embodiment permits clinicians with experience and access to a conventional audiometer (98), to take advantage of the benefits of an ANC audiometer. The next embodiment gives the consumer the opportunity to upgrade their entire audiometer system.

Figure 15:
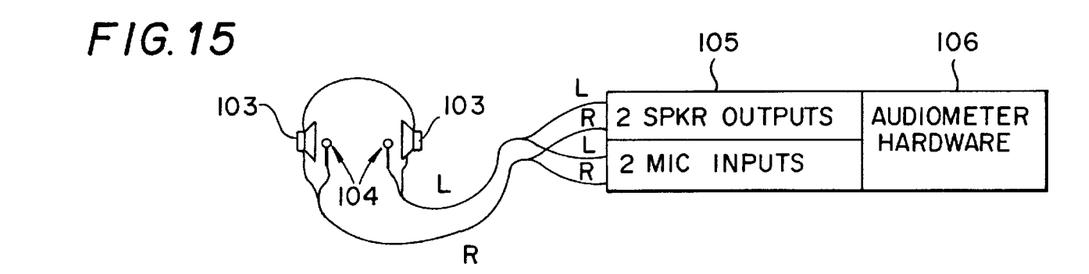
FIG. 15 shows a generalized design for an integrated active noise control audiometer where all of the components required for test stimulus delivery and active noise control are constructed into the same piece of hardware.

An integrated ANC audiometer combines into a single package, both the ANC hardware and audiometry hardware as shown in FIG. 15. In this embodiment, all the functions of the ANC system (105) described above are constructed as integral electronics with the audiometer function electronics (106) within a common casing. The user will be able to switch on or off the ANR functionality depending on the environmental noise conditions. As the test operator switches settings on the audiometer, the ANR circuitry will provide the required additional noise reduction. This integrated configuration of the audiometer can be used as a single unit without need for external attachments of any type. It will require the use of a special headphone system (103)(104) of the construction and functionality described in detail above.

Many new innovations have been discussed in the description of the preferred embodiments presented above. The general concept of using active noise control in audiometry was the focus of the discussion with special emphasis on plant design, controller design, and audiometer/ANC integration. Plant designs which conform to the national and international standards for audiometers were presented as well as designs which may improve attenuation performance but do not fit within these regulations. There are many possible arrangements for the plant but only a few were specifically mentioned. However, the idea of creating a headphone plant which both conforms to standards for audiometers and contains all the necessary components for performing active noise control is novel and innovative even though all possible embodiments are not explicitly described. Alternative plant architectures were described which require their own calibration procedure which was also discussed in detail. Next, several control algorithms were presented in detail, which can be used to perform active noise control on the audiometry system. They include: feedback, feedforward and combined feedback/feedforward. Provisions were made for each of these algorithms to accurately include the audiometry test stimulus allowing a standard calibration procedure to occur. Finally, several embodiments for the combining of the ANC hardware or software with the existing or fabricated audiometer hardware or software were discussed. It will be obvious to those of ordinary skill in the art to make many changes and modifications to the invention without departing from the scope of the appended claims.

What is claimed is:

1. A retrofit active noise control system for use with conventional audiometric hardware in audiometry or hearing acuity testing for attenuating ambient noise in the proximity of the audiometric test subject, said system comprising:
    a means for sensing the ambient noise,
    an attenuation means for attenuating the ambient noise in said proximity of the test subject,
    a control means to adapt said attenuation means so as to reduce said ambient noise in the proximity of the test subject,
    a pre-filter means for calibrating the audiometry test stimulus,
    wherein said control and pre-filter are separate from the conventional audiometric hardware and they connect the said sensing means and attenuation means to the conventional audiometric hardware through said control and pre-filter.

2. The active noise control system as in claim 1 wherein said system incorporates a feedback control means containing analog hardware so as to modify the said attenuation means to attenuate ambient noise.

3. The active noise control system as in claim 1 wherein said system incorporates a feedback control means containing digital software so as to modify the said attenuation means to attenuate ambient noise.

4. The active noise control system as in claim 1 wherein said system incorporates a feedforward control means containing digital software so as to modify the said attenuation means to attenuate ambient noise.

5. The active noise control system as in claim 1 wherein said system incorporates both feedback and feedforward components so as to provide different attenuation means for different ambient noise existing in the proximity of the audiometric test subject, said system comprising.

6. An integrated active noise control system used in conjunction with audiometric or hearing acuity testing equipment which generates a test stimulus while simultaneously attenuating ambient noise existing in the proximity of the audiometric test subject, said system comprising:

a means for sensing the ambient noise, an attenuation means for attenuating the ambient noise in said proximity of the test subject, a control means to adapt said attenuation means so as to reduce said ambient noise in the proximity of the test subject, a pre-filter means for calibrating the audiometric test stimulus, wherein said control and pre-filter are integrated into conventional audiometric hardware having a test stimulus generator such that the said sensing means and attenuation means connect directly to the integrated audiometric hardware.

7. The system as in claim 6 wherein said control means is either analog feedback, digital feedback, feedforward, adaptive feedforward, or adaptive feedback, or any combination thereof.

8. The system as in claim 6 wherein said pre-filter means for calibrating the audiometric test stimulous is the causal inverse of the said attenuation control means thereby delivering the audiometric test stimulous to the said test subject, unaffected by said control means.

* * * * *

UNITED STATES PATENT AND TRADEMARK OFFICE
CERTIFICATE OF CORRECTION

| | |
|---|---|
| PATENT NO. | : 6,396,930 B1 |
| APPLICATION NO. | : 09/026564 |
| DATED | : May 28, 2002 |
| INVENTOR(S) | : Michael Allen Vaudrey and William Richard Saunders |

It is certified that error appears in the above-identified patent and that said Letters Patent is hereby corrected as shown below:

Column 1, line 4, insert the following section title and paragraph before the section entitled "Field of the Invention":

--GOVERNMENT RIGHTS

This invention was made with Government support under contract F41624-97-C-2005 awarded by the Department of the Air Force. The Government has certain rights in this invention. The U.S. Government has a paid-up license in this invention and the right in limited circumstances to require the patent owner to license others on reasonable terms as provided by the terms of contract F41624-97-C-2005 awarded by the Department of the Air Force.--

Signed and Sealed this

Eighth Day of December, 2009

David J. Kappos
*Director of the United States Patent and Trademark Office*